US012611095B2

(12) United States Patent
Do

(10) Patent No.: US 12,611,095 B2
(45) Date of Patent: Apr. 28, 2026

(54) ENDOSCOPE COMPRISING HOLDER FOR INSERTING A LIGHT GUIDE

(71) Applicant: PENTAX MEDICAL BULGARIA LTD., Plovdiv (BG)

(72) Inventor: Anh Minh Do, Munich (DE)

(73) Assignee: PENTAX MEDICAL BULGARIA LTD., Plovdiv (BG)

( * ) Notice: Subject to any disclaimer, the term of this patent is extended or adjusted under 35 U.S.C. 154(b) by 292 days.

(21) Appl. No.: 18/280,813

(22) PCT Filed: Mar. 1, 2022

(86) PCT No.: PCT/EP2022/055056
§ 371 (c)(1),
(2) Date: Sep. 7, 2023

(87) PCT Pub. No.: WO2022/189195
PCT Pub. Date: Sep. 15, 2022

(65) Prior Publication Data
US 2024/0138662 A1 May 2, 2024

(30) Foreign Application Priority Data
Mar. 8, 2021 (DE) .......................... 102021105469.9

(51) Int. Cl.
*A61B 1/07* (2006.01)
*A61B 1/06* (2006.01)
(Continued)

(52) U.S. Cl.
CPC .............. *A61B 1/07* (2013.01); *A61B 1/0669* (2013.01); *A61B 1/0684* (2013.01);
(Continued)

(58) Field of Classification Search
None
See application file for complete search history.

(56) References Cited

U.S. PATENT DOCUMENTS 4,222,629 A * 9/1980 Dassele ................ G02B 6/4292
385/94
4,461,538 A * 7/1984 Breed, III ........... G02B 6/4204
250/227.24
(Continued)

FOREIGN PATENT DOCUMENTS

EP 2624304 A1 8/2013
JP H11-183808 A 7/1999
(Continued)

OTHER PUBLICATIONS

International Search Report issued in WIPO Patent Application No. PCT/EP2022/055056, dated May 23, 2022, along with an English translation thereof.
(Continued)

*Primary Examiner* — John P Leubecker
(74) *Attorney, Agent, or Firm* — GREENBLUM & BERNSTEIN, P.L.C.

(57) ABSTRACT

An endoscope includes a circuit board on which a light source is arranged, a light guide extending in the endoscope, which receives the light from the light source and guides it to an illumination device of the endoscope, and a holder having a light guide hole for inserting the light guide, wherein the cross-section of the light guide corresponds to the cross-section of the light source for optimizing the light transmission.

8 Claims, 12 Drawing Sheets

(51) Int. Cl.
    *F21V 8/00*       (2006.01)
    *G02B 23/24*     (2006.01)

(52) U.S. Cl.
    CPC ........ *G02B 23/2469* (2013.01); *G02B 6/0073* (2013.01); *G02B 6/0091* (2013.01)

(56) References Cited

U.S. PATENT DOCUMENTS

| | | | | |
|---|---|---|---|---|
| 4,826,272 | A * | 5/1989 | Pimpinella | G02B 6/4204 |
| | | | | 257/E33.056 |
| 5,359,208 | A * | 10/1994 | Katsuki | H10F 55/00 |
| | | | | 257/434 |
| 6,821,028 | B2 * | 11/2004 | Morris | G02B 6/4231 |
| | | | | 385/52 |
| 9,360,639 | B2 * | 6/2016 | Choraku | G02B 6/4249 |
| 2003/0042493 | A1 * | 3/2003 | Kazakevich | F21V 13/14 |
| | | | | 257/98 |
| 2005/0013554 | A1 * | 1/2005 | Killer | G02B 6/4243 |
| | | | | 385/88 |
| 2006/0067631 | A1 * | 3/2006 | Wang | G02B 6/4292 |
| | | | | 385/88 |
| 2006/0085969 | A1 | 4/2006 | Bennett et al. | |
| 2007/0153541 | A1 * | 7/2007 | Bennett | A61B 1/00032 |
| | | | | 362/574 |
| 2008/0084683 | A1 | 4/2008 | Takami et al. | |
| 2008/0090090 | A1 | 4/2008 | Munster et al. | |
| 2009/0080214 | A1 | 3/2009 | Watanabe | |
| 2009/0122574 | A1 * | 5/2009 | Ogawa | A61B 1/07 |
| | | | | 362/574 |
| 2011/0026937 | A1 * | 2/2011 | Saitou | G02B 6/4201 |
| | | | | 398/201 |
| 2013/0182099 | A1 | 7/2013 | Nakamura | |
| 2018/0078114 | A1 * | 3/2018 | Kobayashi | A61B 1/00013 |
| 2021/0085160 | A1 * | 3/2021 | Kamee | A61B 1/00016 |
| 2021/0085170 | A1 * | 3/2021 | Ochi | G02B 27/30 |
| 2021/0127960 | A1 * | 5/2021 | Tanaka | A61B 1/0669 |
| 2021/0251471 | A1 * | 8/2021 | Kawahara | A61B 1/0017 |
| 2021/0356730 | A1 * | 11/2021 | Kawahara | A61B 1/00013 |

FOREIGN PATENT DOCUMENTS

| | | |
|---|---|---|
| JP | 2000-266965 A | 9/2000 |
| JP | 2008-090090 A | 4/2008 |
| JP | 2009-072431 A | 4/2009 |
| JP | 2009-118966 A | 6/2009 |
| JP | 2012-200442 A | 10/2012 |
| JP | 2013-034546 A | 2/2013 |
| JP | 2014-147484 A | 8/2014 |
| WO | 2016/189691 A1 | 12/2016 |

OTHER PUBLICATIONS

Notice of Reasons for Refusal issued in Japanese Patent Application No. 2023-543315, dated Dec. 10, 2024, along with an English translation thereof.
Notice of Reasons for Refusal issued in Japanese Patent Application No. 2023-543315, dated Oct. 1, 2024, along with an English translation thereof.

* cited by examiner

ENDOSCOPE COMPRISING HOLDER FOR INSERTING A LIGHT GUIDE

The present invention relates to an endoscope comprising a circuit board on which a light source is arranged, and a light guide extending in the endoscope, which receives the light from the light source and guides it to an illumination device of the endoscope.

The light guide is arranged on the light emission area of the LED to realize the transmission of the light from a light source configured as a LED to the light guide. Normally, the LED is placed on a circuit board.

Thus, the light guide has to be arranged correctly relative to the circuit board.

It is the object of the invention to provide an endoscope where the light guide is advantageously positioned on the circuit board on which a light source is arranged.

This object is achieved by an endoscope comprising the features of claim 1.

Advantageous developments are the subject matter of the dependent claims.

According to the present invention, the endoscope comprises a circuit board on which a light source is arranged, and a light guide extending in the endoscope, which receives the light from the light source and guides it to an illumination device of the endoscope. The endoscope further comprises a holder having a light guide hole for inserting the light guide, wherein the cross-section of the light guide corresponds to the cross-section of the light source for optimizing the light transmission.

Since the cross-section of the light guide corresponds to the cross-section of the light source, the entire cross-section of the light guide can be used for receiving light—if the light guide hole is positioned appropriately relative to the light source. Even the edge portions of the light guide can receive light from the light source without the light source having to have a larger cross-section than the cross-section of the light guide.

In this endoscope, the light guide hole and thus the light guide can be arranged to oppose the light source to optimize light transmission.

The free cross-section of the light guide hole can be approximately equal to the cross-section of the light guide. This allows the light guide to be arranged in the light guide hole such that the light guide maintains its position in the light guide hole. If the light guide remains stationary in the light guide hole, its distance to the light source can be set to a selected advantageous distance which then remains invariable.

The relation of the cross-section of the light guide hole to the cross-section of the light guide can be selected such that a slight press fit of the light guide in the light guide hole is obtained.

The light guide hole can have an opening for such insertion of a plurality of light guides so that the light guides provided in plurality face the light source arranged on a circuit board such that the total cross-section of the light guides provided in plurality and of the light source are approximately equal. Thus, the incidence of light from the light source to the light guides is advantageously designed. Not only the individual light guides in the center of the light guide hole, but also the individual light guides at the edge of the light guide hole can receive light from the light source. Nevertheless, the cross-section of the light source need not be larger than the total cross-section of the individual light guides.

The light source can be an LED. Alternatively, the light source can be an assembly of multiple LEDs. In the assembly of multiple LEDs, the LEDs can be arranged adjacent to each other. Alternatively, in the assembly of multiple LEDs, the LEDs can be arranged to be spaced apart from each other. Furthermore, the light source can include one or more further light guides.

The light guide hole can have a square cross-section. In this case, also the light source has a square cross-section of equal size.

The side of the holder facing the circuit board can be spaced apart from the light source in the portion surrounding the light guide hole. The portion of the holder surrounding the light guide hole opposes the light source. By spacing the light source from the portion of the holder surrounding the light guide hole, it is possible to prevent the light source from being contacted when the holder is mounted. This prevents the light source from being displaced or even damaged. Accidental misplacement of the light source can thus be prevented in a simple and secure manner.

The holder can have a spacer element which protrudes to the side of the circuit board and specifies the distance of the side of the light guide hole facing the circuit board to the light source. The safety of the light source against contact with the holder is thereby ensured in a simple and cost-effective manner.

The holder can include an engaging device that protrudes to the side of the circuit board and engages with an engaging counterpart of the circuit board such that the holder is located integrally on the circuit board. As a result, the mounting of the holder to the circuit board can be performed quickly, easily and still accurately. Mass production is made possible.

The holder can have a light guide hole surrounding portion at the light guide hole, which surrounds the light guide hole, the light guide hole surrounding portion can have a flat surface directed towards the light source, and the light guide can be arranged in the light guide hole such that the end of the light guide directed towards the light source is in alignment with the surface of the light guide hole surrounding portion directed towards the light source.

The flat surface on the holder directed towards the light source provides a reference that predefines the distance to the opposing light source. The light guide merely has to be inserted into the light guide hole such that the end of the light guide directed towards the light source is aligned with the surface of the light guide hole surrounding portion directed towards the light source. Then, the light guide is arranged in the holder such that the distance between light guide and light source corresponds to the desired predefined dimension.

The light guide hole can be centered to the light source. When the light guide hole and thus the light guide are centered to the light source, an optimized light incidence on the light guide can be achieved. The edge of the light guide is then exactly opposed to the edge of the light source.

The aspects of the present invention described above can be suitably combined.

BRIEF DESCRIPTION OF THE DRAWINGS

FIG. 10 shows a distance from the light guide to the light source.

Figure 1:
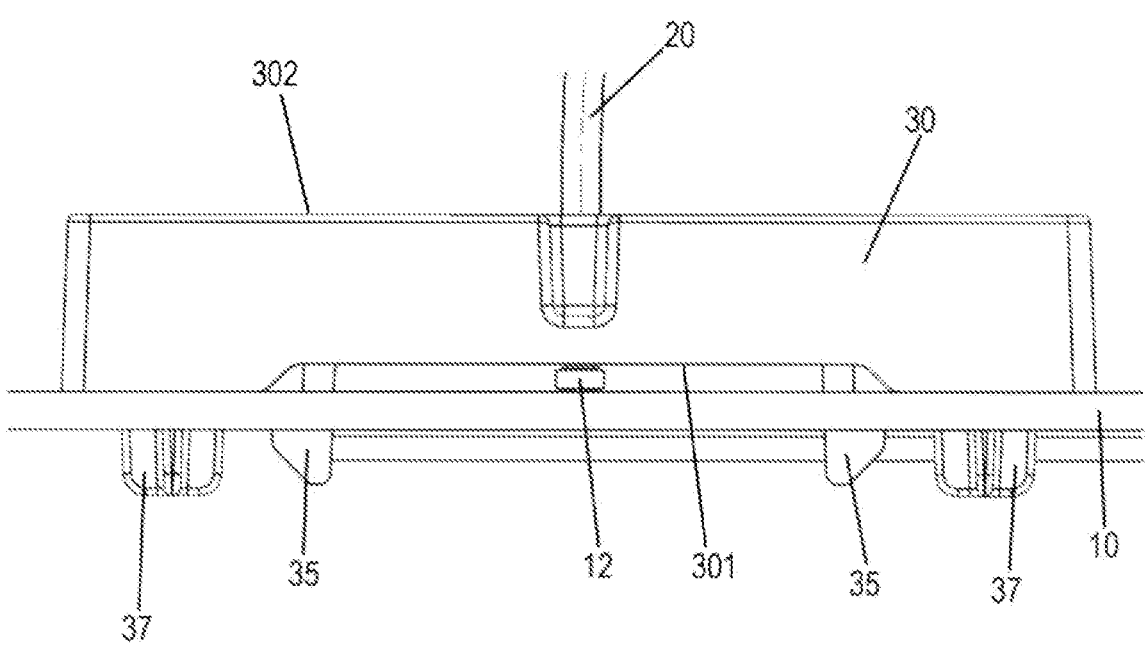
FIG. 1 shows a schematic side view of a holder comprising a circuit board according to the invention in a first embodiment.

The present invention is described in detail below with reference to the drawings on the basis of embodiments. The illustrations in the drawings are not necessarily to scale, but are sometimes shown distorted for reasons of clarity.

First Embodiment

Referring to FIGS. 1 to 13, a first embodiment of the present invention is described below.

An endoscope 100 according to the invention preferably has, at its distal end 13, an illumination device 103 capable of illuminating the surroundings of the endoscope. An illuminated scene can be captured by a camera 105. The camera 105 is arranged on the distal end of the endoscope. In the present embodiment, the light for the illumination device 103 is provided by a light source configured as an LED 12. The light is guided from the LED 12 to the illumination device 103 via light guide 20.

For this purpose, the endoscope according to the invention has, in its interior at a suitable position, e.g. in a control body (not shown), a circuit board 10 on which the LED 12 is arranged.

In the present embodiment, the LED 12 is placed on the circuit board 10 and suitably fixedly arranged. For example, the LED 12 is soldered to the circuit board 10. The LED 12 is arranged on the circuit board 10 such that a light output surface of the LED 12 faces the light guide 20.

For coupling the light emitted from the LED 12, the light guide 20 is held by a holder 30. The holder 30 holds the light guide 20 such that a desired distance dimension between the light guide input surface of the light guide 20 facing the LED 12 and the light output surface of the LED 12 facing the light guide 20 is ensured. In particular, the holder 30 holds an end portion of the light guide 20 directed towards the LED 12 as shown in FIG. 1.

Referring to FIGS. 1 to 5, the holder 30 is described in more detail below.

In the embodiment, the holder 30 has an elongated shape and extends parallel to the circuit board 10 which is also elongated. The holder 30 and the circuit board 10 are not limited to an elongated shape and the details shown in the Figures. The holder 30 has a holder body 31. The holder body 31 has a light guide hole 32, in which the light guide 20 is arranged as described below, extending through the holder body 31. In the present embodiment, the light guide hole 32 forms a centric through hole in the holder body 31. The location of the light guide hole 32 on the holder body 31 can be suitably selected as desired.

Figure 2:
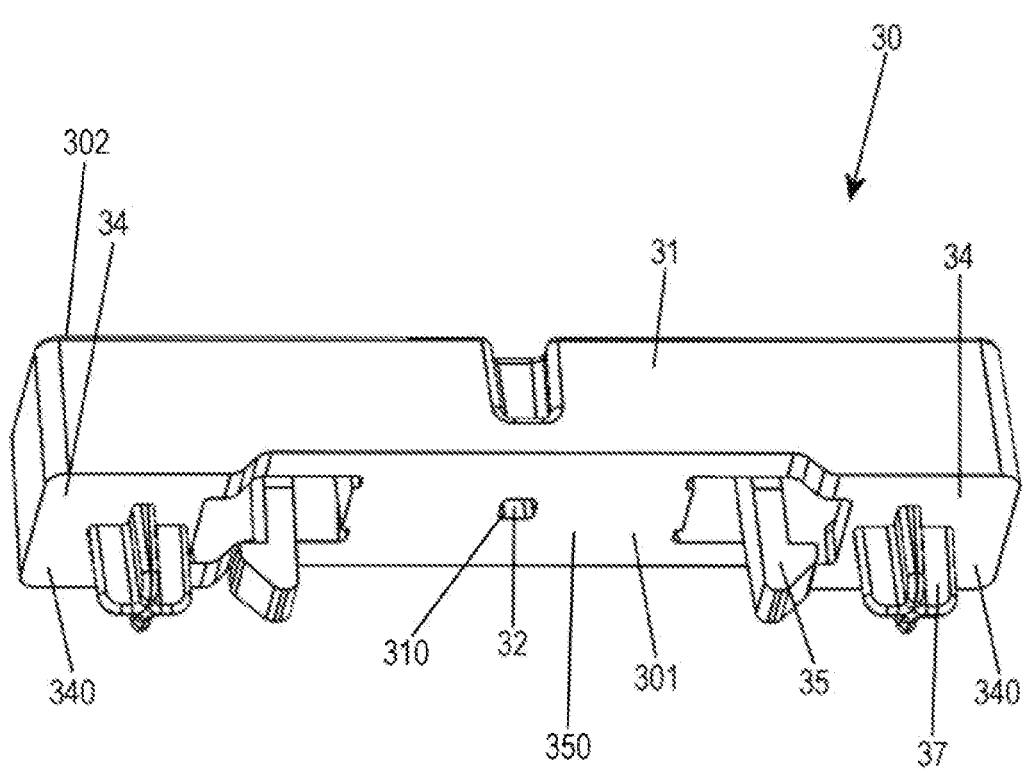
FIG. 2 shows a schematic perspective view of the holder from FIG. 1 from the lower side.
Figure 3:
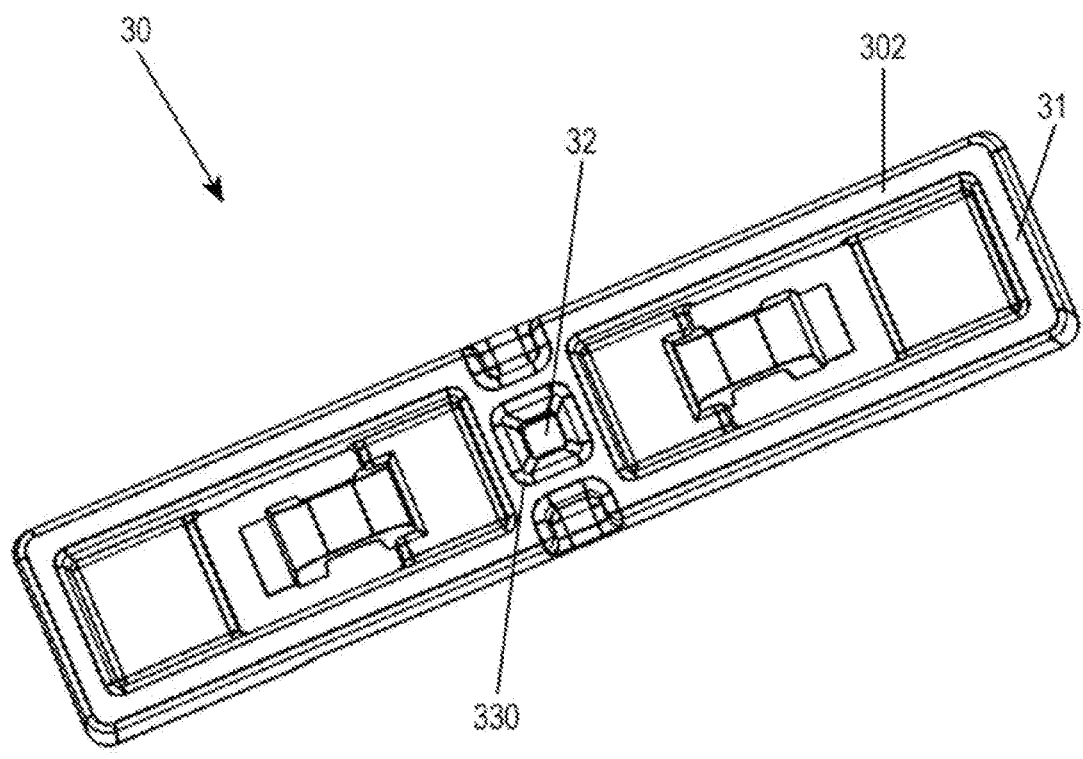
FIG. 3 shows a schematic plan view of the holder.

Thus, the holder body 31 has two sides at which the light guide hole 32 opens into the holder body 31. In particular, the holder body 31 has a respective orifice (opening) 310, 330 of the light guide hole 32 at the outer surface of the holder body 31. One orifice (opening) 310 is located on the side 301 of the holder body 31 facing the circuit board 10, see FIG. 2, and one orifice (opening) 330 is located on the side 302 of the holder body 31 facing away from the circuit board 10, see FIG. 4. In FIGS. 1 and 2, the side 301 of the holder body 31 facing the circuit board 10 forms the lower side of the holder 30; and the side 302 of the holder body 31 facing away from the circuit board 10 forms the upper side of the holder 30. The lower side of the holder 30 is also referred to as circuit board side 301; and the upper side of the holder 30 is also referred to as light guide side 302. In the present embodiment, the circuit board side 301 and the light guide side 302 form opposite sides of the holder 30.

The holder body 31 has at least a protrusion 34 on the circuit board side 301, which protrudes from the holder body 31 to the circuit board 10. In the embodiment, a protrusion 34 is provided on the circuit board side 301 at each longitudinal end of the holder body 31, as shown in FIG. 2. The protrusion 34 has a surface 340 on the circuit board side 301, which serves as a contact surface. The circuit board 10 is in contact with (abuts on) the contact surface 340 in the state in which the holder 30 is fastened to the circuit board 10. Preferably, the contact surface 340 is flat to achieve a favorable contact with (abutment against) the circuit board 10, see FIG. 1. When viewed from the side (FIG. 5), the contact surface 340 is spaced apart from the orifice (opening) 310 of the light guide hole 32 on the circuit board side 301 in the vertical direction (perpendicular to the circuit board 10) with respect to the circuit board 10.

The protrusion 34 functions as a spacer element defining a distance of the orifice (opening) 310 of the light guide hole 32 at the circuit board side 301 to the circuit board 10.

Furthermore, the holder body 31 has on the circuit board side 301 an elastic engagement hook 35 as an engaging device. In the embodiment, two engagement hooks 35 protruding from the holder body 31 to the circuit board 10 are provided. In the embodiment, the engagement hooks 35 are each positioned between the orifice (opening) 310 of the light guide hole 32 and the protrusion 34. The engagement hook 35 is anchored to the holder body 31. Due to its elasticity, the engagement hook 35 can be moved (pivoted) relative to the holder body 31. In the embodiment, the engagement hook 35 has a nose facing away from the orifice (opening) 310 of the light guide hole 32, which can engage with the circuit board 10 as described below.

The holder body 31 further has on the circuit board side 301 an insertion protrusion 37. In the embodiment, two insertion protrusions 37 are provided, which are positioned on the contact surface 340 of the protrusion 34. The insertion protrusions 37 can be tapered (with decreasing external dimension) at the ends facing away from the holder 30. The insertion protrusions 37 can have a rounding at the ends facing away from the holder 30. The insertion protrusions 37 serve to precisely position the holder 30 relative to the circuit board 10.

Thus, in the embodiment, each engagement hook 35 is respectively positioned between the orifice (opening) 310 of the light guide hole 32 and an insertion protrusion 37.

The light guide hole 32 passes through the holder body 31 from the light guide side 302 to the circuit board side 301. In the embodiment, the light guide hole 32 has a square cross-section. The light guide hole 32 has a peripheral wall 320. The light guide hole 32 has an orifice (opening) 310 on the circuit board side 301 and an orifice (opening) 330 on the light guide side 302.

Figure 4:
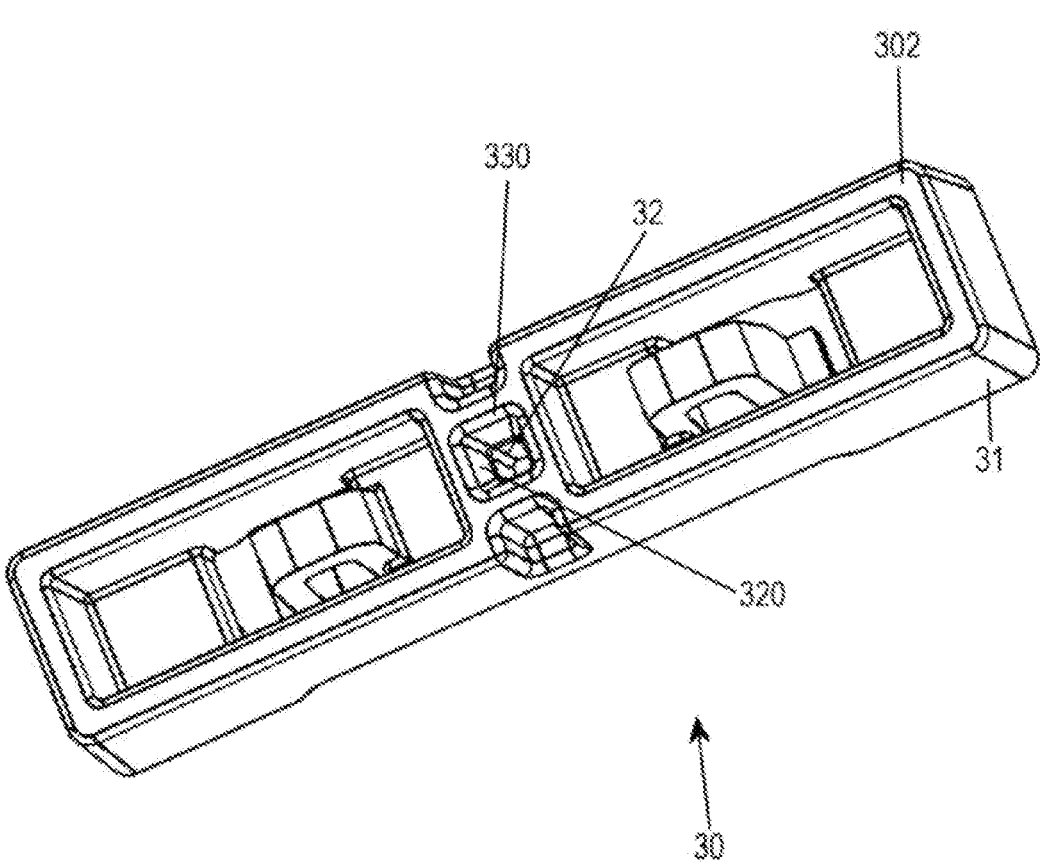
FIG. 4 shows a schematic perspective view of the holder from the upper side.
Figure 5:
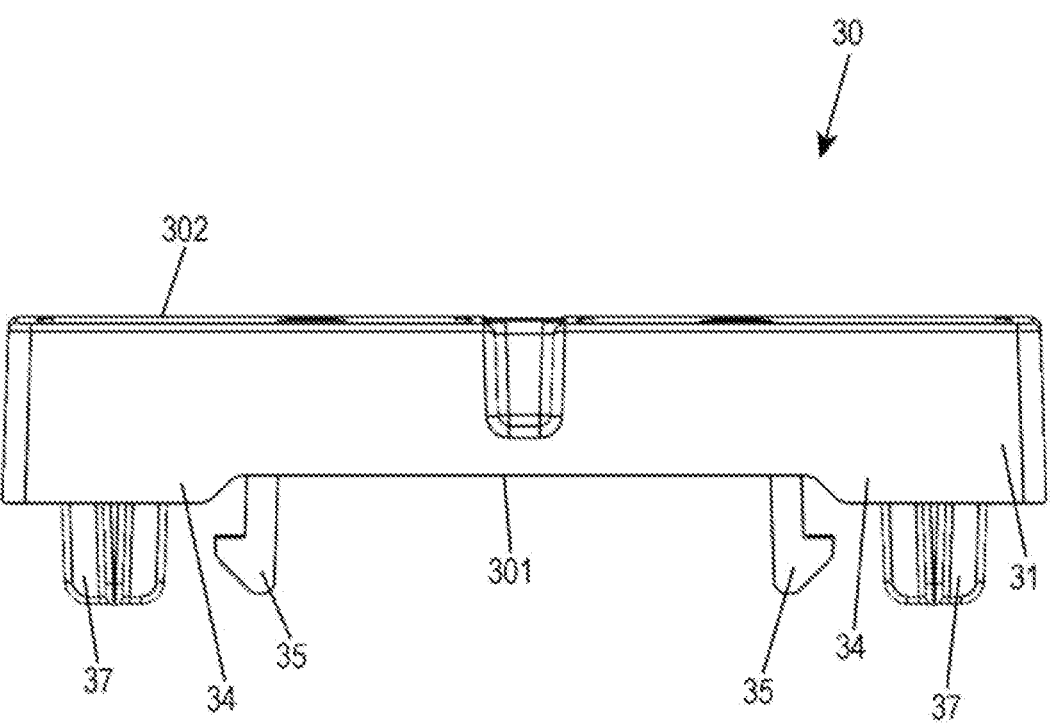
FIG. 5 shows a schematic side view of the holder without a circuit board.
Figure 6:
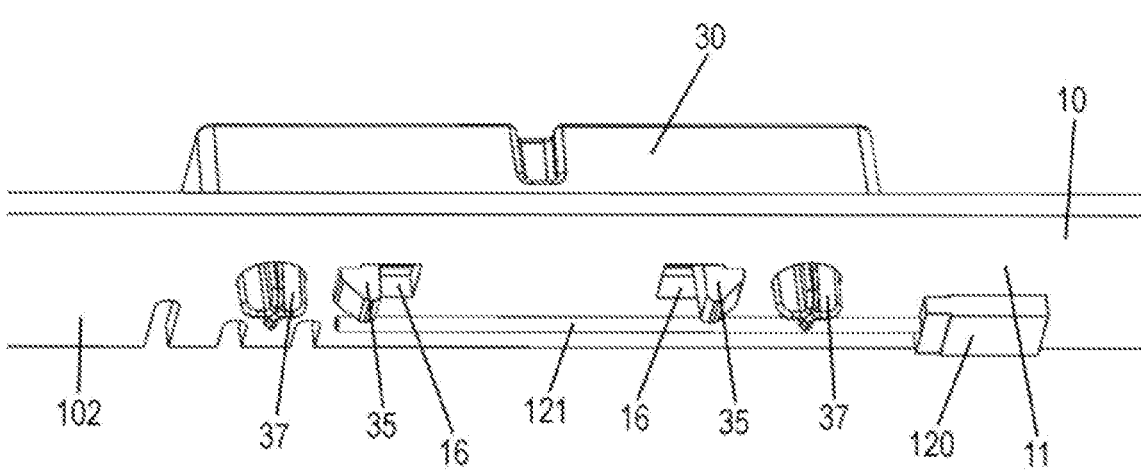
FIG. 6 shows a schematic perspective view from below, where the holder is combined with the circuit board.

The orifice (opening) 330 on the light guide side 302 is beveled (chamfered), see FIG. 4, to facilitate insertion of the light guide 20 from the light guide side 302 and to avoid damage to the end surface of the light guide 20 facing the LED 12.

The orifice (opening) 310 on the circuit board side 301 is not beveled (chamfered), see FIG. 2. The orifice (opening) 310 on the circuit board side 301 is surrounded by a flat (even) surface part 350 that forms a light guide hole surrounding portion. At the orifice (opening) 310, the light guide hole 32 extends perpendicularly (at an angle of 90 degrees) to the surface part 350. The surface part 350 is opposed to the LED 12. In the embodiment, the surface part 350 extends on the circuit board side 301 between the two protrusions 34, see FIG. 2. The surface part 350 has a flat surface directed towards the light source 12.

The arrangement of the light guide 20 in the holder 30 is described below.

Before the holder 30 is attached to the circuit board 10, the light guide 20 is inserted at the holder 30.

The light guide 20 is inserted into the light guide hole 32 from the light guide side 302, and is pushed through the light guide hole 32 until the light guide 20 protrudes on the circuit board side 301 from the orifice (opening) 310 on the surface part 350 towards the LED 12.

Then, by means of a suitable pushing device or manually, the light guide 20 protruding from the orifice (opening) 310 on the surface part 350 is pushed back into the light guide hole 32 until the light guide input surface of the light guide 20 is aligned with the flat surface of the surface part 350 directed towards the LED 12.

This allows a precise definition of the relative position of the light guide input surface of the light guide 20 with respect to the holder 30.

Thereafter, when the holder 30 is attached to the circuit board 10, the relative position and the distance of the light guide input surface of the light guide 20 to the LED 12 arranged on the circuit board 10 are thus precisely defined.

The circuit board 10 is described in more detail below.

Figure 9:
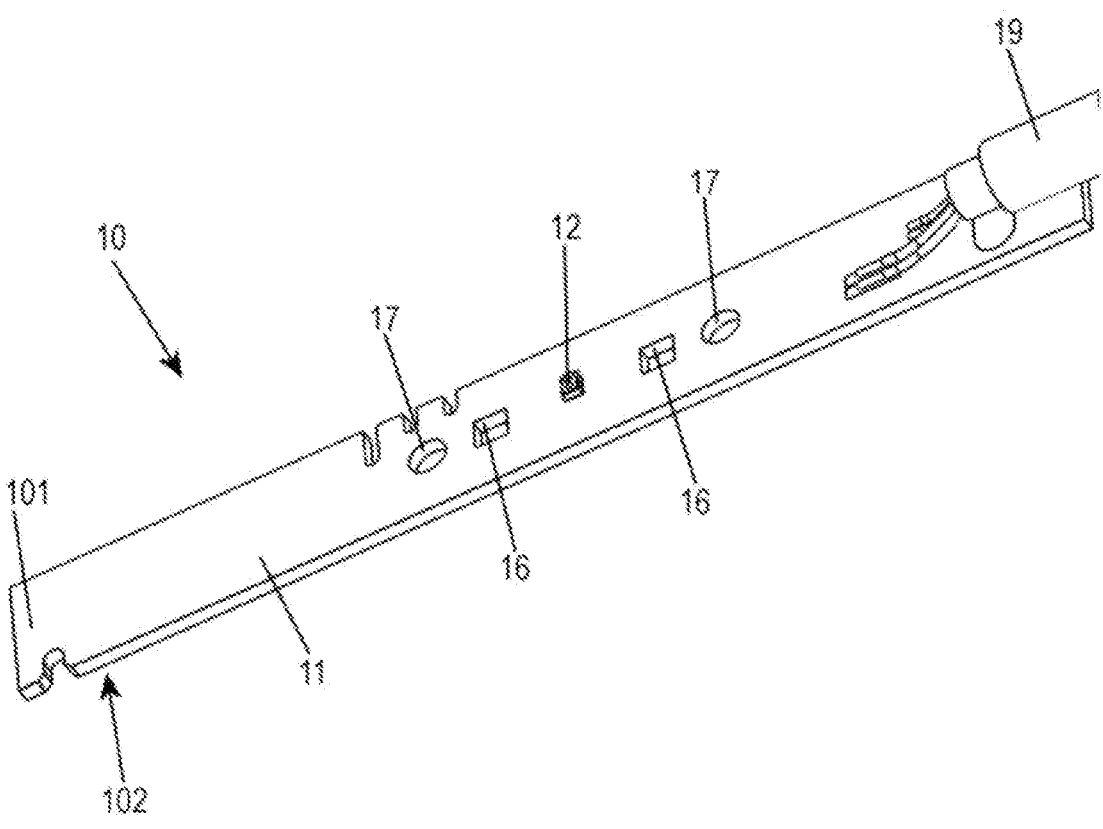
FIG. 9 shows a schematic perspective view of the circuit board.
Figure 10:
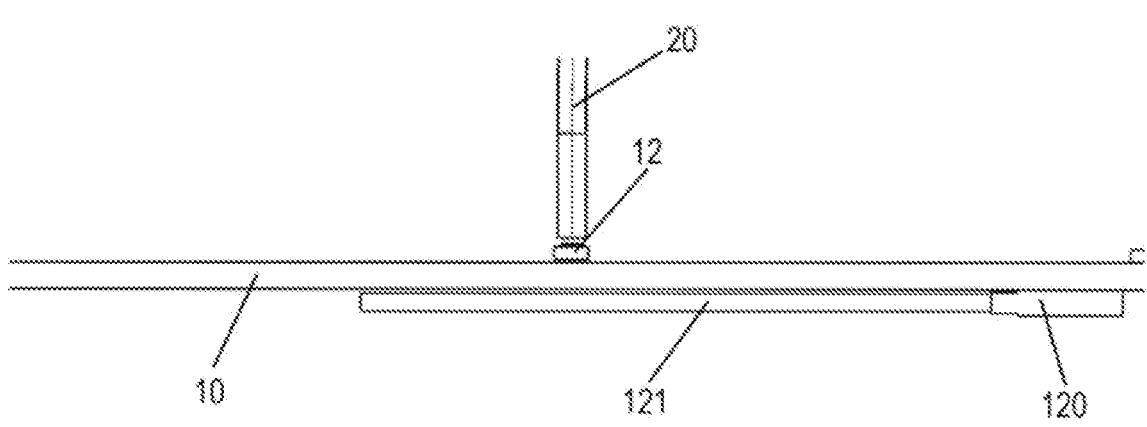
FIG. 10 shows a schematic side view of the positioning of the light guide to the circuit board, with the holder omitted.
Figure 11:
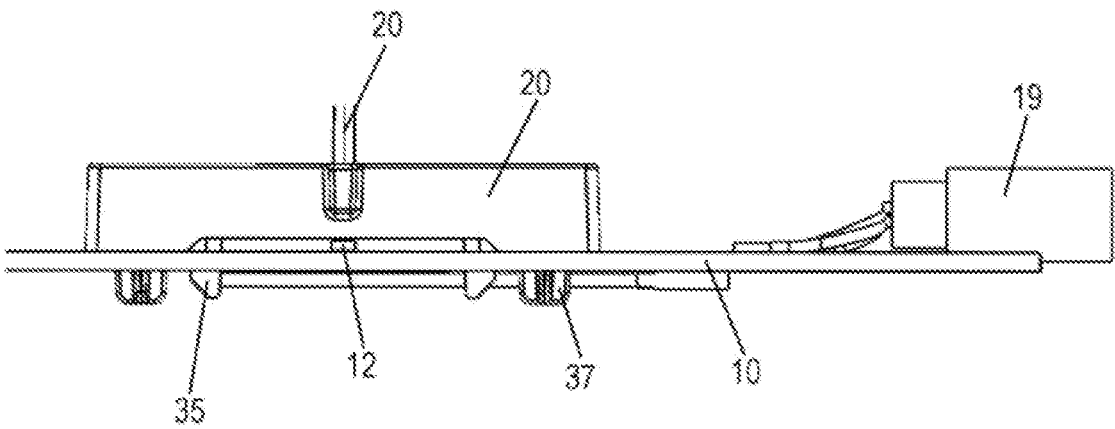
FIG. 11 shows another schematic side view of the holder including the circuit board with a power supply.
Figure 12:
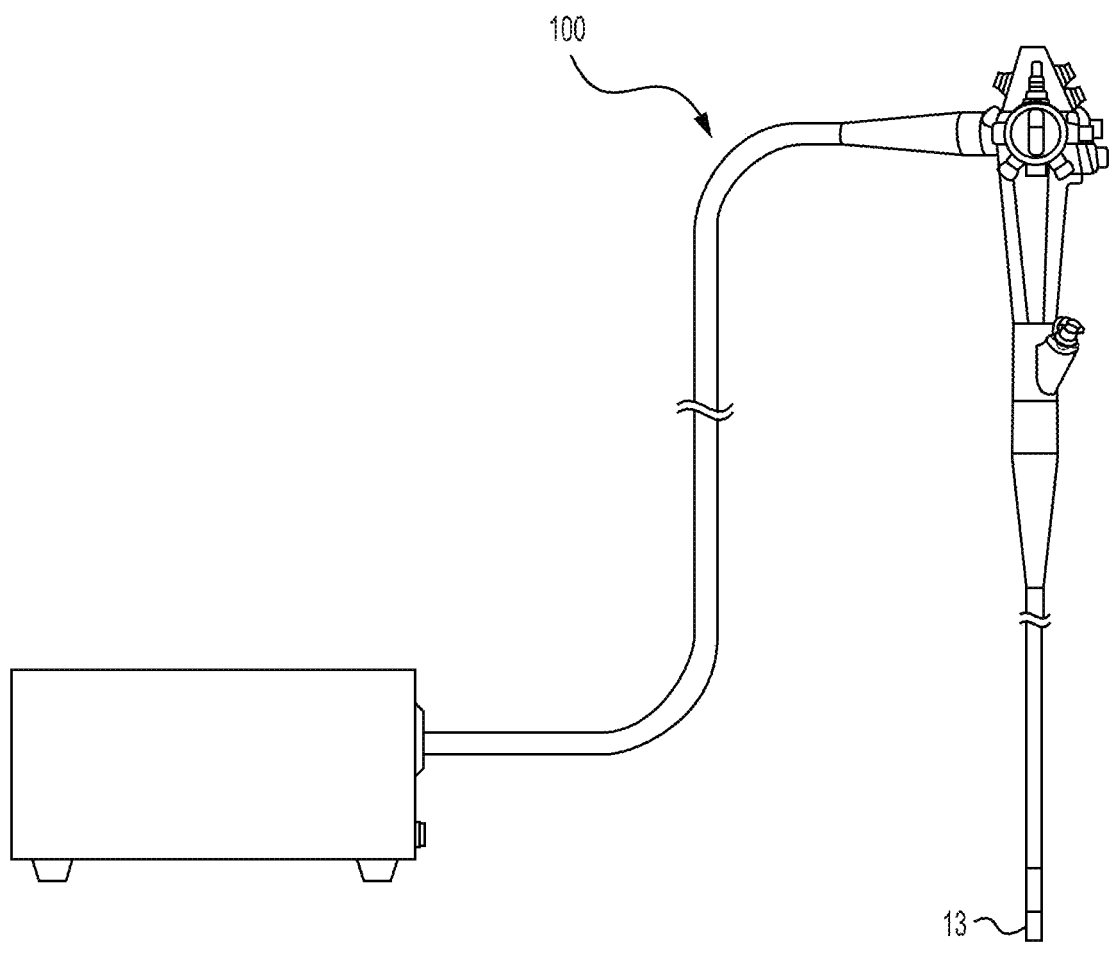
FIG. 12 shows an endoscope according to the invention in a first embodiment.
Figure 13:
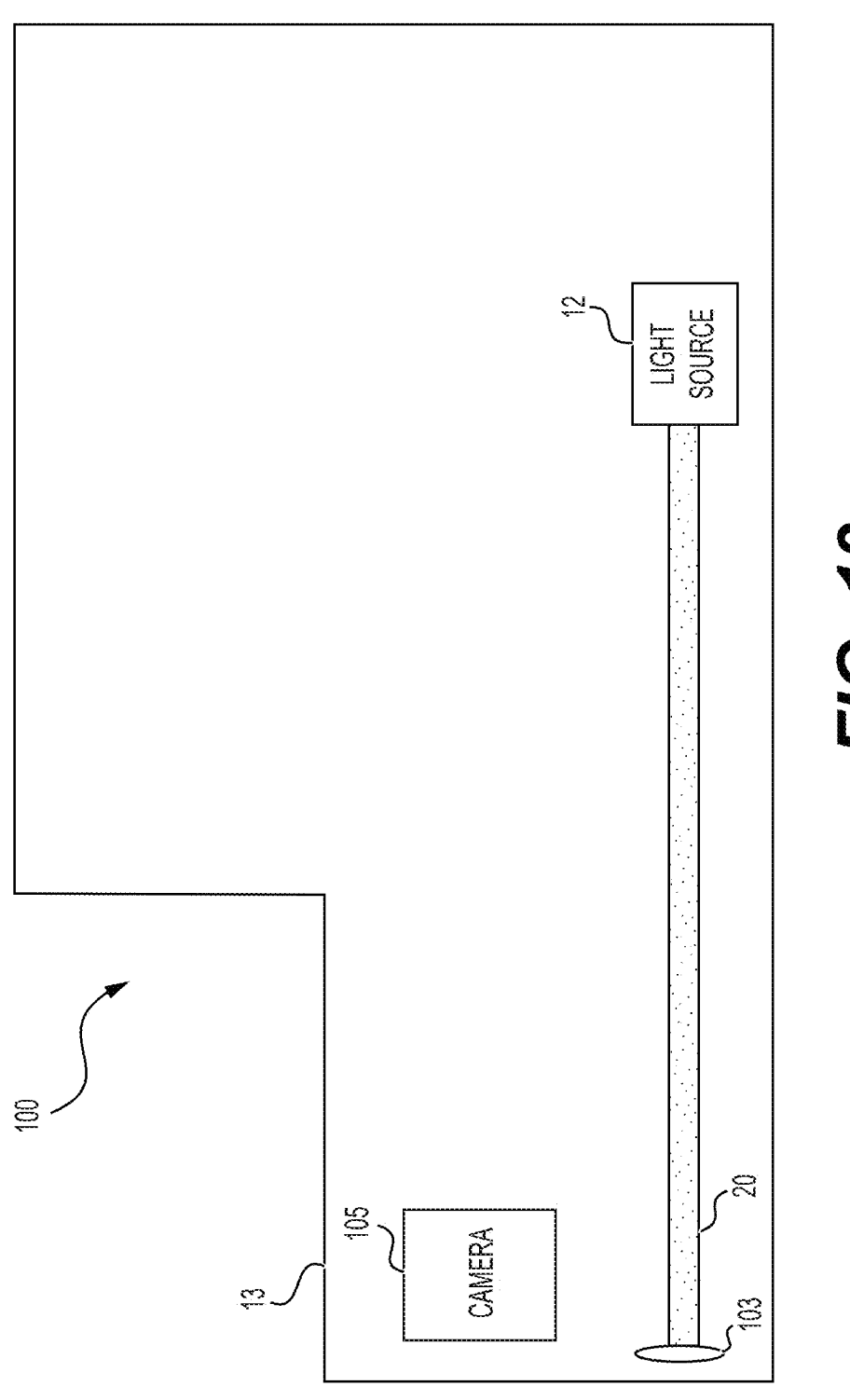
FIG. 13 shows a schematic internal view of the endoscope according to the invention in a first embodiment.

The circuit board 10 is shown in more detail in FIG. 9.

The circuit board 10 has a circuit board body 11 on which the LED 12 is arranged at a suitable position. The circuit board body 11 has an upper side 101 directed towards the holder 30 and a lower side 102 opposite to the holder 30, see FIG. 9.

A suitable conducting path (not shown) is also provided on the circuit board body 11. Furthermore, a supply cable 121 is provided on the circuit board body 11, see FIG. 6. The supply cable 121 is used to supply power and can be routed from a processor (not shown) to the circuit board body 11 and leads into a socket 120. This can be used, among other things, to supply power to the LED 12.

The circuit board 10 can be used for other purposes. Further, on the circuit board body 11, a camera cable 19 can be provided, which comes from the camera arranged on the distal end. The camera cable 19 can be used to supply power to the camera through the supply cable 121 and the socket 120.

An engagement hole 16 is formed as an engaging counterpart on the circuit board body 11 at a position corresponding to the engagement hook 35. The engagement hole 16 is formed such that the engagement hook 35 can be inserted and engaged. The shape of the engagement hole 16 is adapted to the shape of the cross-section of the engagement hook 35. The engagement hole 16 is large enough to allow the engagement hook 35 to be inserted therein and engage its nose on the lower side 102, see FIG. 6 and FIG. 8.

Furthermore, a centering hole 17 is formed on the circuit board body 11 at a position corresponding to the insertion protrusion 37. The insertion protrusion 37 of the holder 30 is inserted into the centering hole 17 to ensure the desired positioning of the holder 30 with respect to the circuit board 10.

Thus, two engagement holes 16 and two centering holes 17 are formed on the circuit board body 11 such that a desired positioning of the holder 30 with respect to the circuit board 10 is obtained.

The desired positioning of the holder 30 with respect to the circuit board 10 is such that the light guide input surface of the light guide 20 is centered with respect to the LED 12, as shown in FIGS. 1, 7, 8 and 10.

The light guide 20 is described in more detail below.

Figure 7:
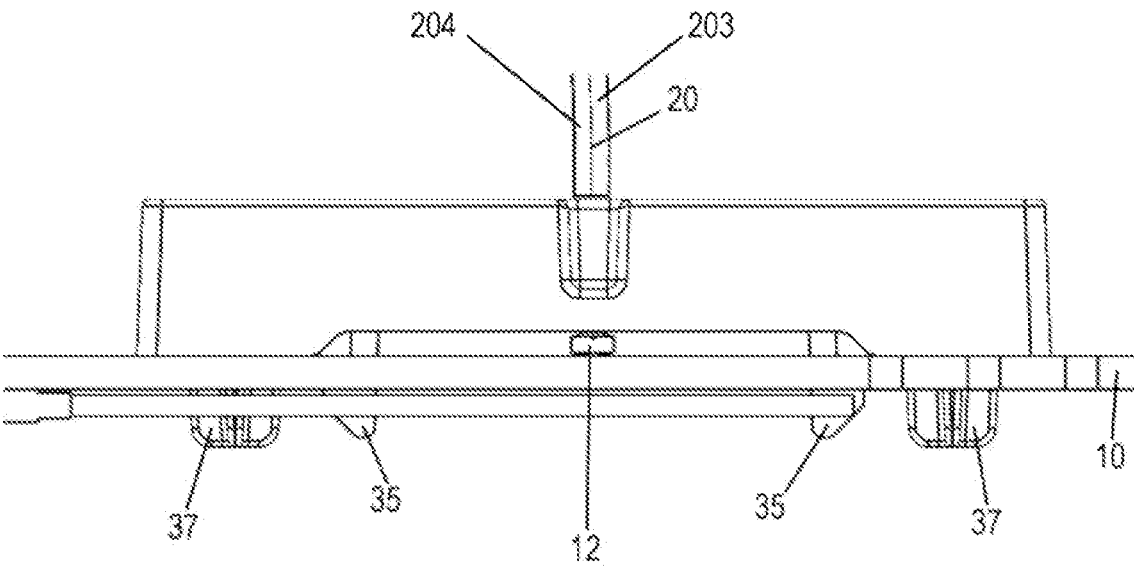
FIG. 7 shows a schematic side view, where the holder is mounted to the circuit board.
Figure 8:
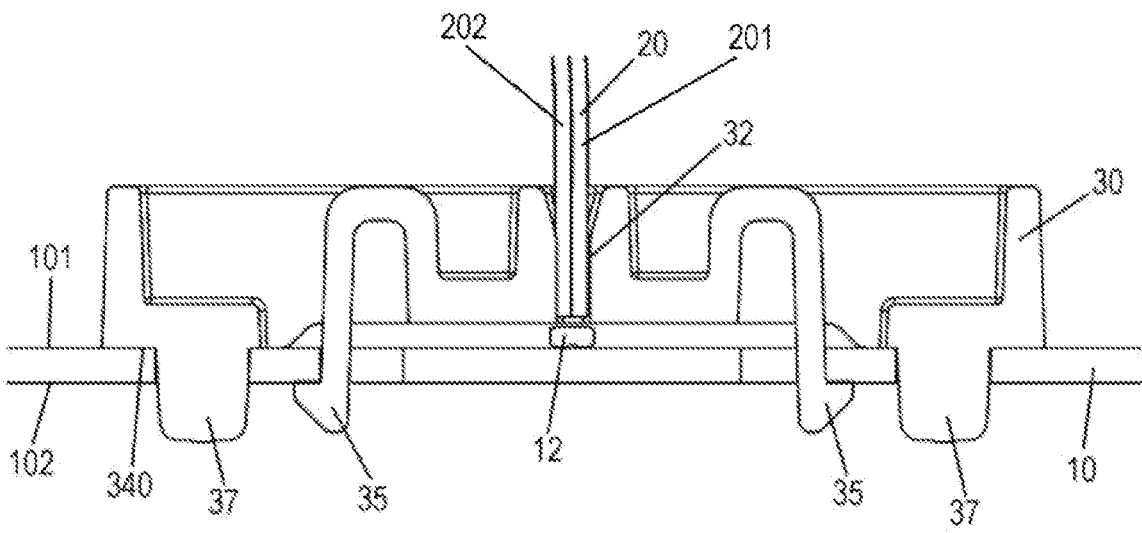
FIG. 8 shows a schematic cross-sectional view, where the holder is mounted to the circuit board. Here, the holder and the circuit board are cut in the longitudinal direction of the holder in the center of the holder.

In the embodiment, the light guide 20 is formed as an approximately square body in cross-section, with the cross-section of the light guide 20 corresponding to the cross-section of the LED 12. The light guide 20 is formed as a bundle of four parallel individual light guides 201, 202, 203 and 204. The four individual light guides 201, 202, 203 and 204 are shown in the FIGS. 7 and 8. The four individual light guides 201, 202, 203 and 204 can each have, for example, a circular or square cross-section, with the exact shape of the cross-section not being limited. FIG. 7 shows a side view of the holder 30, with two individual light guides 203 and 204 arranged on the one (front, i.e. facing the viewer) longitudinal side of the holder 30. FIG. 8 shows a sectional view in the longitudinal direction through the center of the holder 30, with two individual light guides 201 and 202 being arranged on the other (rear) longitudinal side of the holder 30. The four individual light guides 201, 202, 203 and 204 each have the same diameter and contact (abut) each other side by side. Thus, each two of the four individual light guides 201, 202, 203 and 204 are in contact with each other. When viewed in cross-section, an approximately square body therefore results from the four individual cross-sections of the four individual light guides 201, 202, 203 and 204.

The light guide hole 32 is selected to be of such a size that the body of the four individual light guides 201, 202, 203 and 204 is slidable but not loose in the light guide hole 32. The light guide 20 should not be able to slip out of the light guide hole 32 without external influence.

Effect of the Invention

According to the invention, the relative position of the light guide input surface of the light guide 20 to the LED 12 can be precisely defined. The light guide 20 is centered with respect to the LED 12 and the desired distance between the light guide input surface of the light guide 20 and the light output surface of the LED 12 is predefined by the holder 30 at a known height of the LED 12 from the upper side 101 of the circuit board 10.

The relevant cross-sections of the light guide 20 (one light guide or multiple individual light guides) and the LED 12 are approximately equal for optimizing light transmission.

As a result, the light incidence of the light emitted by the LED 12 at the light guide input surface of the light guide 20 is particularly low-loss.

Since the light guide input surface of the light guide 20 and the light output surface of the LED 12 are spaced apart due to the holder 30, even certain occurring tolerances cannot cause the light guide input surface of the light guide 20 to contact the light output surface of the LED 12.

Thus, the structure according to the invention including the holder 30 can be suitably used in mass production.

Correct insertion of the light guide 20 into the holder 30 is simple and quick. Alignment of the light guide input surfaces when using multiple individual light guides can be ensured in a simple and safe manner.

Due to the shape and size of the light guide hole 32 adapted to the light guide 20 or the multiple individual light guides, the light guide 20 sits sufficiently firmly and securely in the light guide hole 32.

The engagement function allows the holder 30 to be easily and securely attached to the circuit board 10.

The predefined distance between the light guide input surface of the light guide 20 and the light output surface of the LED 12 can range from 0.001 mm to 10 mm, for example.

Alternatives

In the embodiment, the holder 30 is shown in a cuboid shape. The shape of the holder 30 is not limited and can be chosen as desired.

In the embodiment, the circuit board side 301 and the light guide side 302 form opposite sides of the holder 30, but the invention is not limited thereto. In an alternative, the light guide side 302, as the side where the light guide hole 32 has the orifice (opening) 330 for inserting the light guide 20, may be a lateral surface of the holder 30; and the circuit board side 301 forms the lower side of the holder 30, as in the embodiment. In this variant, the light guide hole 32 does not extend straight as in the embodiment, but has an arcuate shape.

The protrusion 34 as a spacer element can be omitted when the LED 12 is embedded in the circuit board 10. The spacing dimension between the light guide input surface of the light guide 20 facing the LED 12 and the light output surface of the LED 12 facing the light guide 20 can be adjusted by the embedding depth of the LED 12 in the circuit board 10.

In the embodiment, the contact surface 340 is flat so that the circuit board 10 is in contact therewith (abuts thereon). Alternatively, the contact surface 340 can be uneven (have protrusions and recesses). Then, when viewed in the direction perpendicular to the circuit board 10, the distance between the LED 12 and the end of the light guide 20 facing the LED can be adjusted based on the configuration of the distance dimension between the point of surface 340 protruding farthest toward the circuit board and the light guide hole surrounding portion adjacent to the light guide hole 32.

In the embodiment, the light guide 20 is spaced apart from the light output surface of the LED 12. In an alternative, the light guide 20 can contact (abut on) the light output surface of the LED 12 by appropriately selecting the protrusion amount of the protrusion 34 from the holder body 31.

The number and structure of the engagement hooks 35 and engagement holes 16 can be selected arbitrarily.

The number and structure of the insertion protrusions 37 and centering holes 17 can be selected arbitrarily.

In the embodiment, the engagement hooks 35 are each positioned between the orifice (opening) 310 of the light guide hole 32 and the protrusion 34, and the insertion protrusion 37 is respectively formed on the protrusion 34. The exact location of both the engagement hook 35 and the insertion protrusion 37 can also be selected at other positions on the holder body 31.

In the embodiment, the surface part 350 extends on the circuit board side 301 between the two protrusions 34. Alternatively, the surface part 350 can protrude from the lower side 301 of the holder 30 to the LED 12. In this variant, the protrusion protruding to the LED 12 is formed at the lower side 301 of the holder 30, the light guide hole 32 extending in the protrusion and being open towards the LED 12. Thus, the side of this protrusion directed towards the LED 12 includes the orifice (opening) 310 and a flat surface surrounding the orifice (opening) 310.

The number of individual light guides in the light guide 20 is not limited. The light guide 20 can comprise a single individual light guide or a suitable plurality of individual light guides. A suitable plurality of individual light guides is obtained when the individual light guides arranged parallel to each other form an approximately square shape in the overall cross-section, to which the shape of the light guide hole 32 is adapted. For example, a suitable plurality of individual light guides can comprise a matrix array of individual light guides each having an equal number of rows and columns. When the light guide 20 is a single individual light guide, its cross-section can be square or circular.

The formulation "the cross-section of the light guide corresponds to the cross-section of the light source" also includes the case of a light guide having a circular cross-section which corresponds to a square cross-section of the light source in terms of size.

LIST OF REFERENCE SIGNS

10 circuit board
11 circuit board body
12 LED (light source)
16 engagement hole (engaging counterpart)
17 centering hole
19 camera cable
20 light guide
30 holder
31 holder body
32 light guide hole
34 protrusion (spacer element)
35 engagement hook (engaging device)
37 insertion protrusion
101 upper side of the circuit board
102 lower side of the circuit board
120 socket
121 supply cable
201 individual light guide
202 individual light guide
203 individual light guide
204 individual light guide
301 lower side of the holder (circuit board side)
302 upper side of the holder (light guide side)
310 orifice (opening) of the light guide hole 32 on the circuit board side 301
320 peripheral wall of the light guide hole
330 orifice (opening) of the light guide hole 32 on the light guide side 302
340 contact surface

350 surface (surface part) opposed to the LED adjacent to the light guide hole (light guide hole surrounding portion)

The invention claimed is:

1. An endoscope comprising:

a circuit board on which a light source is arranged;

a light guide extending in the endoscope and which receives light from the light source and guides it to an illumination device of the endoscope; and a holder having a light guide hole for inserting the light guide, wherein a cross-section of the light guide corresponds to a cross-section of the light source, the holder comprising:

a spacer which protrudes toward a side of the circuit board and fixes the distance of a side of the light guide hole facing the circuit board to the light source, the spacer including an insertion protrusion configured to position the holder relative to the circuit board; and an engaging hook which protrudes toward the side of the circuit board, the engaging hook having a nose configured to extend through and engage an underside of the circuit board such that the holder is fixed to the circuit board, the engaging hook positioned between the light guide hole and the spacer.

2. The endoscope according to claim 1, wherein a cross-section of the light guide hole is approximately equal to the cross-section of the light guide.

3. The endoscope according to claim 1, wherein the light guide hole has an opening for insertion of a plurality of light guides so that the light guides provided in plurality face the light source arranged on the circuit board such that a total cross-section of the light guides provided in plurality and of the light source are approximately equal.

4. The endoscope according to claim 1, wherein the light source is an LED.

5. The endoscope according to claim 1, wherein the light guide hole has a square cross-section.

6. The endoscope according to claim 1, wherein a side of the holder facing the circuit board is spaced apart from the light source in a portion surrounding the light guide hole.

7. The endoscope according to claim 1, wherein at the light guide hole, the holder has a light guide hole surrounding portion that surrounds the light guide hole, the light guide hole surrounding portion has a flat surface directed towards the light source, and the light guide is arranged in the light guide hole such that an end of the light guide directed towards the light source is in alignment with the surface of the light guide hole surrounding portion directed towards the light source.

8. The endoscope according to claim 1, wherein the light guide hole is centered to the light source.

\* \* \* \* \*